United States Patent [19]

Carr

[11] Patent Number: 4,967,006
[45] Date of Patent: Oct. 30, 1990

[54] COPRODUCTION OF PROPANEDIAMINE AND ALKYLATED AMINOPROPYLAMINES

[75] Inventor: Richard V. C. Carr, Allentown, Pa.

[73] Assignee: Air Products and Chemicals, Inc., Allentown, Pa.

[21] Appl. No.: 334,848

[22] Filed: Apr. 7, 1989

[51] Int. Cl.$^5$ .................. C07C 209/26; C07C 209/48; C07C 209/60
[52] U.S. Cl. .................................. 564/490; 558/452; 558/455; 564/491
[58] Field of Search ....................... 564/490, 491, 473; 558/455, 462, 452

[56] References Cited

U.S. PATENT DOCUMENTS

| | | | |
|---|---|---|---|
| Re. 23,124 | 6/1949 | Gresham | 260/584 |
| 2,045,574 | 6/1936 | Adkins et al. | 260/128 |
| 2,349,461 | 5/1944 | Pratt et al. | 260/583 |
| 2,448,013 | 8/1948 | Buc et al. | 260/465.5 |
| 2,452,602 | 11/1948 | Robinson, Jr. | 260/583 |
| 2,579,580 | 12/1951 | Howk | 260/465.1 |
| 3,119,872 | 2/1964 | Scott | 260/583 |
| 3,180,853 | 4/1965 | Peters, Jr. | 260/77.5 |
| 3,280,074 | 10/1966 | McCaleb et al. | 260/47 |
| 3,427,356 | 2/1969 | Baer et al. | 260/583 |
| 3,522,309 | 7/1970 | Kirby | 260/577 |

*Primary Examiner*—Richard L. Raymond
*Assistant Examiner*—P. O'Sullivan
*Attorney, Agent, or Firm*—Russell L. Brewer; James C. Simmons; William F. Marsh

[57] ABSTRACT

This invention relates to a process for the coproduction of propanediamines and alkylated aminopropanediamines. The process contemplates an initial cyanoethylation of ammonia under conditions for producing aminopropionitrile and modest levels of iminobispropionitrile. After separation of the iminobispropionitrile from the aminopropionitrile, the process involves the catalytic reductive alkylation of the iminobispropionitrile by reaction with an aldehyde in the presence of hydrogen to form the alkylated iminobispropionitrile followed by the catalytic hydrogenation of the nitrile group in aminopropionnitrile and iminobispropionitrile to the amine.

4 Claims, No Drawings

COPRODUCTION OF PROPANEDIAMINE AND ALKYLATED AMINOPROPYLAMINES

TECHNICAL FIELD

This invention relates to a process for the coproduction of propanediamines and alkylated iminobispropylamines.

BACKGROUND OF THE INVENTION

Propanediamine and alkylated iminobispropylamines such as methyliminobispropylamines are known compositions and have been used in the manufacture of chelating agents and in paper applications as a wet end additive.

The following patents are representative of various processes to produce aliphatic and cyclic polyamines:

U.S. Pat. No. 2,452,602 discloses a process for producing aliphatic polyamines by reacting an unsaturated aldehyde with ammonia in the presence of hydrogen. In this reaction, a conventional hydrogenation catalyst, e.g., Raney nickel catalyst, is used to enhance the condensation of the aldehyde with ammonia to produce the aliphatic amine. A specific example shows the production of n-butylamine by reaction of crotonaldehyde with ammonia in the presence of hydrogen.

U.S. Pat. No. 2,349,461 discloses procedures for producing secondary and tertiary amines by reacting an aldehyde or ketone with ammonia in the presence of hydrogen and a hydrogenation catalyst and by reducing alkylcyanides with hydrogen in the presence of hydrogenation catalyst. To produce secondary or tertiary amines the patentees react hydrogen at an elevated temperature with a mixture containing a nitrile, alcohol, aldehyde or ketone in the presence of a hydrogenation catalyst. Diethylamine is prepared by reacting acetonitrile with acetaldehyde in the presence of hydrogen.

U.S. Pat. No. 3,522,309 discloses a process for the reductive alkylation of amines to produce N-alkylated amines. In this process, ammonia or primary and secondary amines are contacted with a carbonyl compound, e.g., an aldehyde, in the presence of a hydrogenation catalyst, e.g., a platinum or palladium metal on a support.

U.S. Pat. No. 3,119,872 discloses a process for producing aliphatic 1,3-diamines by reacting an alpha-beta-unsaturated aldehyde or ketone with ammonia or primary amine and then catalytically hydrogenating the condensation product.

U.S. Pat. No. 2,579,580 discloses the cyanoethylation of organic compounds containing labile hydrogen atoms, such as amines, amides, and ketones. The cyanoethylation reaction is carried out in the presence of a cross-linked polyquaternary ammonium hydroxide resin.

U.S. Pat. No. 2,045,574 discloses the process for producing amines by contacting a carbonyl compound with ammonia or an amine with hydrogen in the presence of a hydrogenation catalyst.

Re. No. 23,124 discloses the process of producing N-dimethylethanolamines by alkylating cyanhydrins. The alkylation is effected by contacting the cyanhydrin with an aldehyde in the presence of hydrogen and a hydrogenation catalyst, e.g., a nickel, cobalt or nickel-cobalt catalyst system.

It is also know from the prior art that 1,3-propanediamine can be prepared by cyanoethylation of ammonia followed by catalytic hydrogenation of the resulting nitrile. This reaction typically results in the production of a by-product, namely, iminobispropionitrile. This is due to the inherent over-cyanoethylation of ammonia which then on hydrogenation forms iminobispropylamine. Alkylation of the iminobispropylamine results in a variety of by-products.

SUMMARY OF THE INVENTION

This invention relates to a selective process for the coproduction of propanediamines and alkylated iminobispropylamines. This improved process contemplates the cyanoethylation of ammonia by reaction of ammonia with acrylonitrile to produce aminopropionitrile as well as iminobispropionitrile. The iminobispropionitrile is separated from the aminopropionitrile and then reductively alkylated by reaction with an aldehyde in the presence of hydrogen and a hydrogenation catalyst under reductive alkylation conditions. The resulting alkylated iminobispropionitrile, as well as the initial aminopropionitrile, then is catalytically hydrogenated under conditions for effecting reduction of the cyano groups to the primary amine.

There are several significant advantages associated with the coproduction process described herein. First the reaction is highly selective to the formation of propanediamines and alkylated iminobispropylamines. Second it utilizes relatively low mole ratios of ammonia to acrylonitrile in the cyanoethylation step, thus minimizing the amount of ammonia that has to be recovered on separation, and third it minimizes the level of acrylonitrile used to produce alkylated iminobispropionitriles. The reduced level of acrylonitrile in the product alleviates substantial separation and recovery steps not to mention distillation costs.

DETAILED DESCRIPTION OF THE INVENTION

The improved process for the coproduction of propanediamines and alkylated iminobispropylamines is achieved through the selective combination of several process steps.

The first step in the process involves the cyanoethylation of ammonia to produce aminopropionitrile. Inherent in the cyanoethylation reaction is the coproduction of iminobispropionitrile which is the reaction product of 2 moles acrylonitrile per 1 mole of ammonia. In order to limit the level of iminobispropionitrile produced in the process, the mole ratio of ammonia to acrylonitrile is maintained at a high level, vis-a-vis the acrylonitrile. For purposes of practicing the first step in the process, the cyanoethylation is carried out using a mole ratio of ammonia to acrylonitrile to about 5 to 15:1. Although higher molar ratios of ammonia to acrylonitrile can be utilized in the system to enhance the selectivity to aminopropionitrile, the greater the ratio of ammonia to acrylonitrile the greater the amount of unreacted ammonia which must be recovered for commercial feasibility of the process. Even so, at such high mole ratios of ammonia to acrylonitrile, substantial levels of iminobispropionitrile are produced. The initial cyanoethylation step employs a temperature of from 30°C. to 90°C., and a pressure of from 120 to 500 psig. Reaction times vary, but typically, reaction times will range from about 30 to 180 minutes.

Subsequent to the formation of aminopropionitrile and iminobispropionitrile, the products are separated, e.g., by distillation wherein ammonia is vented from the system and recovered and the aminopropionitrile separated from iminobispropionitrile. Separation is important to minimize the degree of by-product formation in the following steps.

To produce the alkylated iminobispropionitriles, iminobispropionitrile is contacted with an alkylating agent, i.e., a $C_1$–$C_6$ aldehyde under reductive alkylation conditions. Aldehydes suited for use in reaction with the iminobispropionitrile for effecting reductive alkylation therein include formaldehyde, acetaldehyde, propionaldehyde, butyraldehyde, isobutyraldehyde, etc. Alpha-beta ($C_{3-6}$) unsaturated aldehydes can also be used, e.g., crotonaldehyde, etc. Although the derivatives are slightly different than are those prepared with the saturated aldehydes.

The key to high selectivity to propanediamines and alkyl iminobispropylamines in the process is in selectively effecting reductive alkylation of the iminobispropionitrile while minimizing the level of catalytic hydrogenation of the nitrile and thus the formation of the amine. Once reductive alkylation is complete, reductive alkylation of the thus-formed amine can be effected. This two step process is in contrast to the prior art in that the prior art reactions carried out an in-situ catalytic hydrogenation of the nitrile followed by the reductive alkylation of the amine formed with the aldehyde. Such processes would not be operative in this program iminobispropylamine by-product formation.

Catalytic reductive alkylation of the iminobispropionitrile with the aldehyde is effected by contacting the iminobispropionitrile with the aldehyde in the presence of hydrogen using a highly active hydrogenation catalyst, e.g., platinum or palladium carried on a support. The use of a less active hydrogenation catalyst, e.g., Raney nickel or cobalt or silica or alumina may tend to effect hydrogenation of the nitrile to form the amine which then may undergo alkylation with the aldehyde, thereby resulting in substantial by-product formation.

To enhance selectivity during reductive alkylation, the reaction temperature is maintained from about 50°C. to 135°C., preferably from 80°C. to 120°C. and relatively low pressures. e.g., pressures in the range of from 50 to 250 psig. A mole ratio of from about 0.95 to 1.15 moles aldehyde/mole nitrile is used. Reaction times are maintained at modest levels, e.g., 6 to 10 hours.

The final step in the process resides in the catalytic reduction of the nitrile groups present in aminopropionitrile to form 1,3-propanediamine and reduction of the cyano group in the alkylated iminobispropionitrile to form the alkylated bispropylamine. Catalytic hydrogenation of the nitrile is carried out under conventional conditions, e.g., the temperature is maintained at about 50°C. to 120°C. and hydrogen pressures from 400 to 2000 psig using a hydrogenation catalyst. The hydrogenation catalyst typically is a Raney nickel or cobalt catalyst system carried on a support. Hydrogenation of a nitrile to the amine is known and procedures such as those described in U.S. Pat. No. 4,137,267 can be used and are incorporated by reference.

The following examples are provided to illustrate various embodiments of the invention and are not intended to restrict the scope thereof.

EXAMPLE 1

Cyanoethylation of Anhydrous Ammonia and Separation of the APN/IBPN Product Mixture To a one liter stainless steel autoclave was added 408 (27.1 moles) of anhydrous ammonia. The contents were heated to 50°C. and then 214.5 g (4.04 moles) of acrylonitrile were added continuously to the autoclave over a period of one hour. The reaction mixture was stirred an additional one hour at 50°C. (autogenous pressure 306–329 psig) and then the contents were cooled and unreacted ammonia vented. About 266 g of a clear colorless liquid was recovered which analyzed by gas chromatography to be 39.1 wt % aminopropionitrile (APN) 59.3 wt % iminobispropionitrile (IBPN), and 1.6 wt % miscellaneous heavies. This material was distilled to remove APN in 99.5% purity (GC analysis)., a 96% recovery was achieved (58–62°C. @8.5 torr). The dark brown distillation residue analyzed to be 94.2 wt % IBPN, 1.93 wt % APN, and 3.87 wt % miscellaneous heavies.

This example shows even at the high mole ratio of ammonia to acrylonitrile (7:1) substantial cyanoethylation of APN occurred resulting in large quantities of iminobispropionitrile.

EXAMPLE 2

Reductive Methylation of Iminobispropionitrile

A 300 cc Hastelloy C autoclave was charged with 10.0 g of 5% palladium on carbon catalyst (50 wt % water wet). The reactor was flushed several times with nitrogen and then hydrogen. Then 123 g of crude IBPN obtained as the distillation residue in Example 1 was pumped into the autoclave. The temperature of the reactor contents was raised to 95°C. and hydrogen was added to provide a pressure of 115 psig. Formaldehyde (as a 55 wt % solution in methanol) was then admitted to the autoclave at a rate of 0.2 ml/min until a total of 66.9 g had been added. The mixture was allowed to react for 3.5 hours at which time analysis by gas chromatography/mass spectroscopy revealed that the IBPN had been completely converted to methyliminobispropionitrile (MIBPN). The reactor contents containing the MIBPN were then cooled and filtered and the methanol and water were removed in vacuo to give a clear light yellow liquid. Little to no reduction of the nitrile to the amine occurred under these conditions as evidenced by the lack of terminal N-methyl derivatives in the GC mass spectrum.

EXAMPLE 3

Hydrogenation of MIBPN

A 300 cc Hastelloy C autoclave was charged with 10.0 g of a commercial Raney nickel catalyst, i.e., Raney nickel 2800. The reactor was flushed several times with nitrogen and then hydrogen and 23 g of ammonia were added after addition of hydrogen and ammonia, 20 ml of methanol were added to the autoclave. The temperature of the reactor contents was raised to 95°C. and the pressure was raised to 810 psig by addition of hydrogen. Approximately, 100 g (0.73 moles) of the reaction mixture containing MIBPN from Example 2 added continuously over a period of 3.5 hours. At this point, the hydrogen uptake was about 85% of that required for the hydrogenation of the nitrile. The reaction was allowed to go to completion overnight and then the reactor contents were cooled, and the reactor vented. The contents were filtered to remove the catalyst. A clear, light yellow liquid product was obtained and when analyzed by gas chromatography was found to consist of 69.8 wt % methyliminobispropylamine (MIBPA), 4.9 wt % MAPA and 25.2 wt % miscellaneous heavies. Thus the IBPN obtained as a distillation residue from Example 1 was ultimately converted to MIBPA via selective reductive methylation to MIBPN followed by hydrogenation of MIBPN to MIBPA. Only because the reductive methylation procedure was sufficiently mild as to preclude reduction of the nitrile group was the procedure viable to produce the valuable MIBPA product.

EXAMPLE 4

Reductive Methylation of Distilled Iminobispropionitrile

Into a 100 ml stainless steel autoclave was placed 2.62 g of 5% palladium on carbon (50% water wet) catalyst. The reactor was flushed several times with nitrogen and then with hydrogen. Then 30 g of distilled IBPN was added to the reactor. The reactor contents were heated to 90°C. and the pressure raised by addition of hydrogen to 118 psig. Formaldehyde (as a 55 wt % solution in methanol) was added to the stirred reactor continuously over a period of six hours. The reaction was continued another hour at which point analysis of a sample by gas chromatography revealed that the IBPN had been entirely consumed and the mixture was analyzed and was found to contain 96.9 wt % MIBPN, 1.2 wt % 3,3-dimethylaminopropionitrile, and 1.9 wt % N-methoxmethylaminobispropionitrile.

EXAMPLE 5

Reduction of 3-aminopropionitrile

Into a 100 ml stainless steel autoclave is placed 1.26 g of Raney nickel 2800. The reactor was flushed several times with nitrogen, hydrogen, and then 19.0 g of anhydrous ammonia was admitted to the reactor. The reactor was then charged with 25.3 g of 3-aminopropionitrile. With agitation, the solution was warmed to 92°C. and the pressure adjusted to 800 psig with hydrogen.

After a reaction period of 6 hours, hydrogen uptake ceased. Analysis of the reaction product by GC revealed the crude product mixture to be comprised of 91.8 wt % 1,3-propanediamine, 7.1 wt % iminobispropylamine, and 1.1 wt% propylamine.

What is claimed is:

1. In a process for producing propanediamine by the cyanoethylation of ammonia followed by the catalytic reduction of the nitrile group to the amine, the improvement for coproducing alkylated iminobispropylamine which comprises:

effecting cyanoethylation of ammonia by reaction of ammonia with acrylonitrile utilizing a mole ratio of ammonia to acrylanitrile from 5-15:1 under conditions for forming aminopropionitrile and iminobispropionirile;

separating aminopropionitrile from iminobispropionitrile generated in the cyanoethylation of ammonia;

contacting the iminobispropionitrile with a $C_{1-6}$ alkylaldehyde in the presence of hydrogen under conditions for effecting reductive alkylation of the iminobispropionitrile and ineffective for effecting substantial hydrogenation of the nitrile group to form the corresponding iminobispropylamine;

contacting the alkylated iminobispropionitrile with hydrogen in the presence of a hydrogenation catalyst under conditions effective for reducing the nitrile groups to the amine forming alkylated iminobispropylamine; and contacting the aminopropionitrile with hydrogen in the presence of a hydrogenation catalyst under conditions effective for reducing the nitrile group to the amine, and thereby forming propanediamine.

2. The process of claim 1 wherein the aldehyde used as the alkylating agent is formaldehyde.

3. The process of claim 2 wherein the catalyst used for reductive alkylation contains palladium as an active metal.

4. The process of claim 3 wherein the reductive alkylation is carried out at a temperature of from 50°C. to 135°C., a pressure from 50 to 250 psig and the mole ratio of aldehyde to iminobispropionitrile is from about 0.95 to 1.15:1.

* * * * *